United States Patent [19]

Hubbard et al.

[11] 4,385,950

[45] May 31, 1983

[54] SMALL ICE PACKS AND METHOD OF MANUFACTURING THE SAME

[75] Inventors: Vance M. Hubbard, Euless; Welton K. Brunson, Bedford, both of Tex.

[73] Assignee: Tecnol, Inc., Fort Worth, Tex.

[21] Appl. No.: 408,637

[22] Filed: Aug. 16, 1982

Related U.S. Application Data

[62] Division of Ser. No. 184,466, Sep. 5, 1980, Pat. No. 4,347,848.

[51] Int. Cl.³ .................... A61F 7/10; B32B 31/18
[52] U.S. Cl. .................... 156/73.1; 156/250; 156/267; 156/308.4; 493/195; 493/200
[58] Field of Search ............... 156/73.1, 73.3, 250, 156/267, 269, 308.4, 510, 580.1, 580.2, 251; 128/399, 402, 403; 493/200, 203, 195

[56] References Cited

U.S. PATENT DOCUMENTS

| 3,356,086 | 12/1967 | Behney | 128/402 |
|---|---|---|---|
| 3,491,761 | 1/1970 | Baker | 128/402 |
| 3,607,521 | 9/1971 | Suominen et al. | 156/250 |
| 3,749,620 | 7/1973 | Montgomery | 156/73.1 |
| 3,893,834 | 7/1975 | Armstrong | 128/403 |
| 4,149,541 | 4/1979 | Gammons et al. | 128/402 |

Primary Examiner—Michael G. Wityshyn
Attorney, Agent, or Firm—Jerry W. Mills

[57] ABSTRACT

The specification discloses a refillable sanitary ice pack (10) for single patient use. The ice pack takes the form of a generally rectangular envelope (12) having two sides (14, 16), an open end (18) and a closed end (20). Two pairs of tie strings (22, 24) and (26, 28) extend from the open and closed ends, respectively. A bag (30) closed on three sides and having a throat (34) opening at the open end of the envelope is formed internally of the envelope for receiving and retaining ice. A funnel (38) dimensioned to conform with the divergence of the throat in the bag may be inserted into the throat for filling the bag. A closure member (50) is also provided for sealing the throat of the bag when the bag has been filled with ice.

2 Claims, 5 Drawing Figures

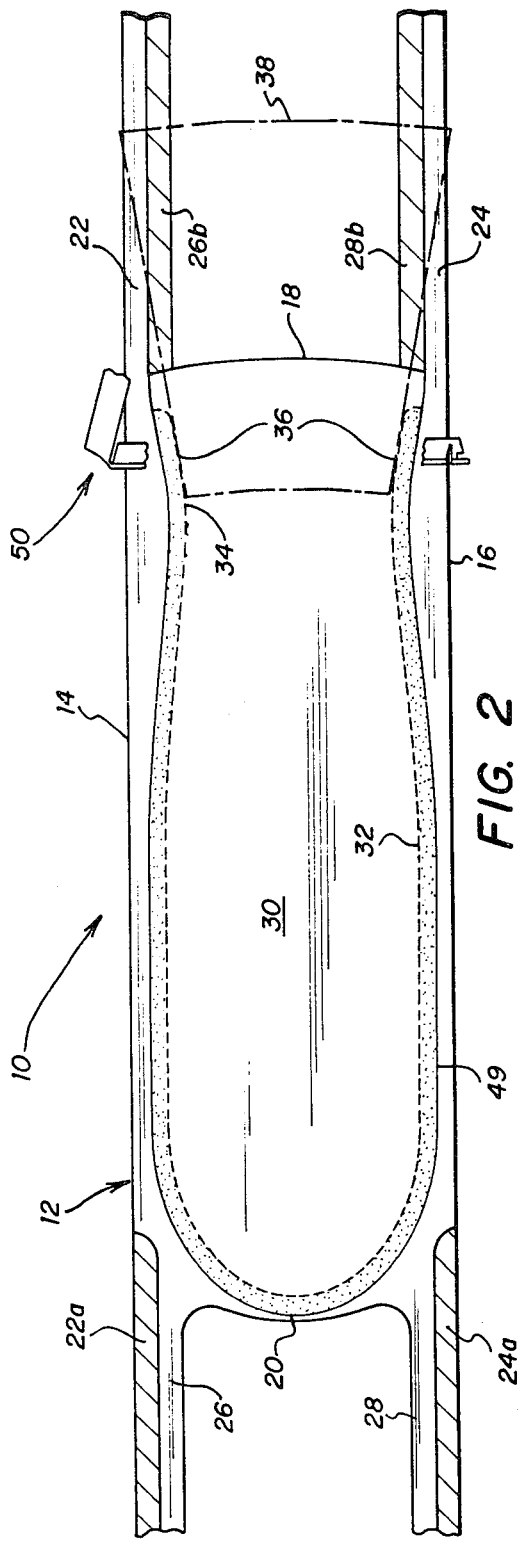
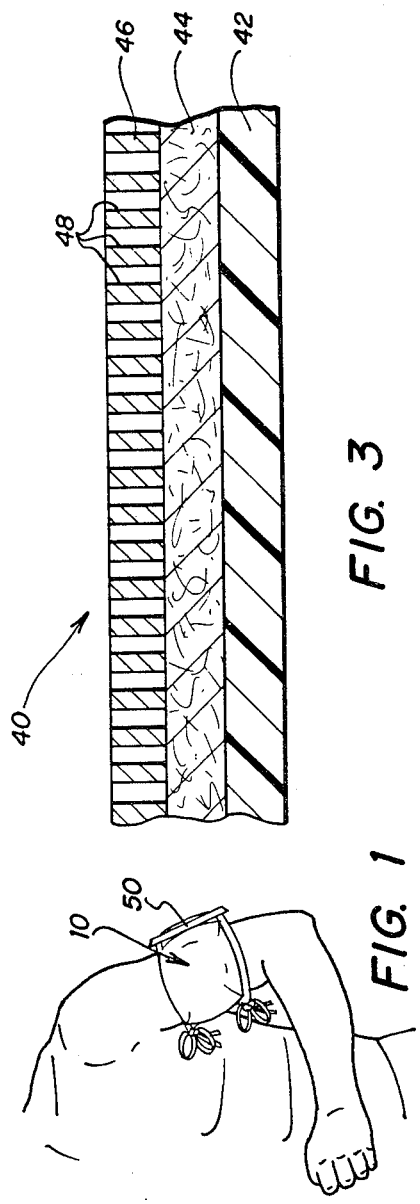
FIG. 2
FIG. 3
FIG. 1

SMALL ICE PACKS AND METHOD OF MANUFACTURING THE SAME

This is a divisional of application Ser. No. 184,466 filed Sept. 5, 1980, now Pat. No. 4,347,848.

TECHNICAL FIELD

This invention relates to medical devices and more particularly to improvements in small ice packs designed for single patient use.

BACKGROUND ART

Ice packs for single patient use are generally of two types: large general purpose ice packs designed for application to large areas of the body and small, specialized ice packs designed for application of cold locally at particular points. These smaller ice packs, because of their size, typically have small openings, which are difficult to fill from an automatic ice machine or from a scoop from an ice bin, and which often result in the spillage of ice during filling and damage to the disposable ice packs which tend to be of more fragile construction.

Sanitation considerations also limit the use of the ice packs in hospitals and clinics. Many small ice packs, for example, designed for single patient use, must be disposed of after single use due to the likelihood of contamination of the ice machine or scoop with an ice pack which has been in contact with a patient's body, or there is risk of contaminating the ice supply. This is both expensive and wasteful. Accordingly, a need arises for a small, single patient ice pack which can be easily filled and refilled from an automatic ice machine or scoop without contamination of the source of ice and damage to the ice pack. More efficient methods of constructing small ice packs and devices for maximizing single patient use are likewise needed.

DISCLOSURE OF THE INVENTION

In accordance with one aspect of the invention, a refillable, sanitary ice pack for single patient use is disclosed. The ice pack contains a generally rectangular envelope having an open end and a closed end and containing a waterproof bag member formed internally thereof, opening at the open end of the envelope. The envelope is formed of a three ply material containing an inner layer of waterproof material, an intermediate layer of absorbent material, and an outer layer of absorbent material perforated by a multitude of tiny holes. A first pair of tie strings extend longitudinally of the envelope from the open end and a second pair of tie strings extend longitudinally of the envelope from the closed end. A closure member is employed for selectively sealing the bag member after filling with ice. The closure member has a blade-like member and a sheath member hingedly connected thereto for compressing the envelope against the blade-like member when the blade member is inserted into the sheath member.

According to a second aspect of the invention, an ice pack having a generally rectangular envelope is provided having an open end and a closed end and having a waterproof bag member formed internally therein. The bag member is closed on three sides and has an outwardly diverging throat opening at the open end of the envelope. The ice pack has a first pair of tie strings extending longitudinally of the envelope from the open end and a second pair of tie strings extending longitudinally of the envelope from the closed end. A disposable funnel, dimensioned to be inserted into the throat of the bag member, is provided for facilitating the filling of the ice pack. The funnel is dimensioned to converge at its lower end at substantially the same angle as the diverging throat of the bag member. A closure member, dimensioned to be disposed adjacent the open end of the envelope, is provided for selectively sealing the throat of the bag member when filled with ice. The closure member contains a blade-like member and a sheath member hingedly connected thereto. The blade-like member is dimensioned to seal the throat when the envelope is folded over the blade-like member and the blade-like member is enclosed in the sheath member.

According to a third aspect of the invention, a closure member is provided for selectively sealing a small ice pack. The closure member includes a substantially planar elongate blade-like member having inwardly tapered end surfaces and a rib extending substantially the length of the blade-like member along the base thereof. One of the tapered end surfaces contains a notch formed internally thereof and a cut formed in the base proximate the notched surface such that the notched end surface may be compressed inwardly of the blade-like member when the blade-like member is enclosed in the sheath member. The sheath member, dimensioned to receive the blade-like member, is provided with two substantially parallel sidewalls, the sidewalls containing a plurality of longitudinal ribs extending the length thereof. The sidewalls define open, outwardly tapered end surfaces dimensioned to conform substantially to the end surfaces of the blade member, the length of the sheath member being slightly less than the blade member such that the notched end surfaces of the blade-like member are compressed inwardly of the blade-like member when the blade-like member is forced into the sheath member. A flexible member connecting the end surface of the sheath member to the unnotched end surface of the blade-like member is provided to permit the blade-like member to be selectively moved into and out of registration with the sheath member. The sheath member also contains a flange disposed along the base thereof extending outwardly of the end surfaces dimensioned to engage the notched end surface of the blade-like member to lock the blade-like member into registration with a sheath member.

BRIEF DESCRIPTION OF DRAWINGS

FIG. 1 is a perspective view of the improved small ice pack, showing the ice pack and clamp in use on the arm of a patient;

FIG. 2 is a plan view of the improved small ice pack showing the bag, the closure member and the funnel inserted in the bag;

FIG. 3 is a magnified section view of the material from which the ice pack is constructed;

DETAILED DESCRIPTION

Figure 4:
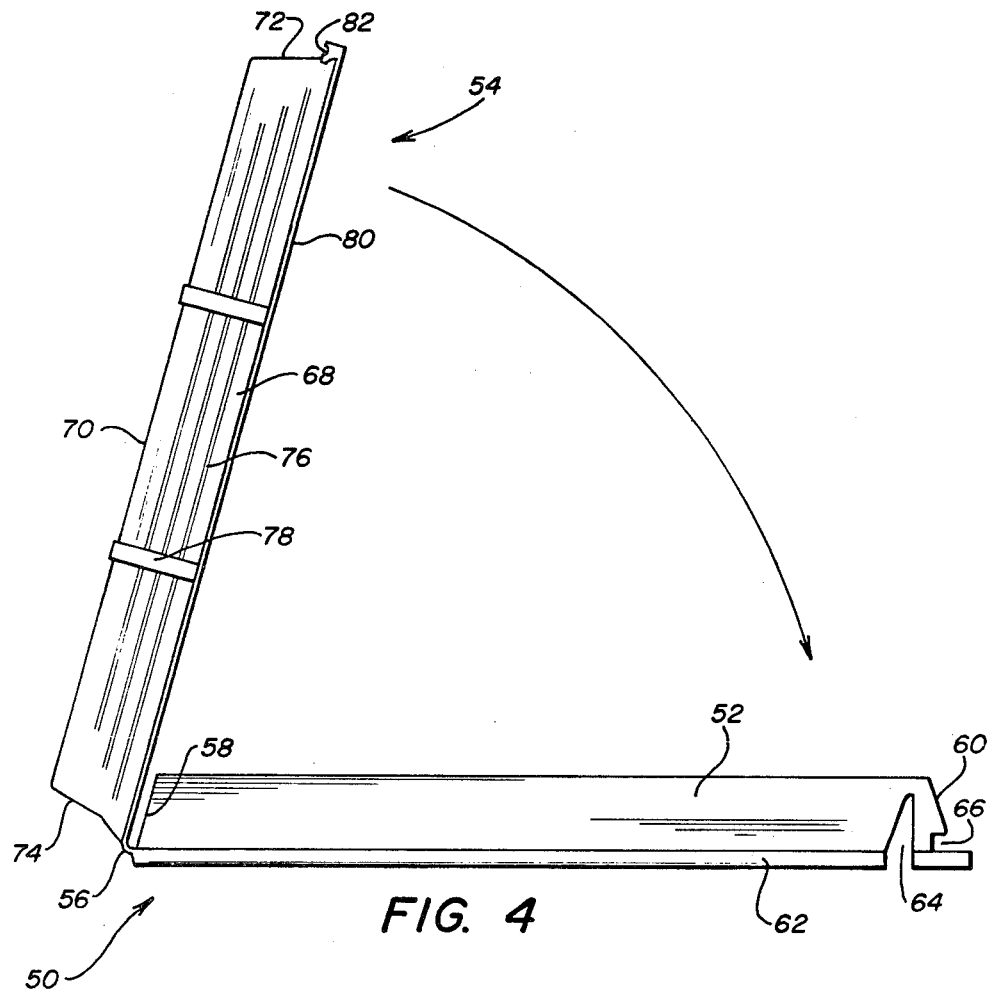
FIG. 4 is a plan view of the closure member.

FIG. 1 shows the small improved ice pack 10 of the present invention in actual operation. In this particular application, the ice pack is fastened to the arm of a patient by means of a pair of tie strings extending from each end thereof, as shown in greater detail in FIG. 2. A closure member 50 is also shown in its closed operational position whereby it seals the open end of the ice pack.

Referring now to FIG. 2, the small ice pack 10 of the type commonly employed for single patient use in the application of cold to small areas of the body is shown in greater detail. Ice pack 10 includes a generally rectangular envelope 12 having sides 14 and 16, an open end 18 and a closed end 20. A first pair of tie strings 22 and 24 extend outwardly of open end 18 parallel to sidewalls 14 and 16. A second pair of tie strings 26 and 28 likewise extend outwardly of closed end 20 parallel to sidewalls 14 and 16, but are offset inwardly from the strings 22 and 24 a distance equal to their width to permit construction of another ice pack from the same material with minimum use of fabric in accordance with the method that will be hereafter described.

A waterproof bag 30 made of polyethylene or other inexpensive waterproof material is formed internally of ice pack 10, as shown by the broken line in FIG. 2, bag 30 being sealed along its edges as indicated by the seam 32 and having a throat 34 opening outwardly of open end 18. As best seen in FIG. 2, throat 34 has diverging walls 36 which diverge at substantially the angle of convergence of a disposable funnel 38 employed in connection with the ice pack 10. Disposable funnel 38, shown in phantom in FIG. 2, is inserted in throat 34 to facilitate filling of the bag and to permit refilling of the bag without contaminating the source of ice when the ice pack is brought into direct contact with the source of ice. Substantial correspondence between the tapering walls of funnel 38 and the taper of sidewalls 36 is important for uniform distribution of the load in the funnel since disposable ice packs are typically and preferably made of relatively fragile material subject to tearing and rupture.

FIG. 3 illustrates in magnified cross section, the material from which the ice pack is constructed. The innermost layer of material is a thin sheet of polyethylene 42. Layer 42 is bonded to an intermediate layer of absorbent material 44 which in turn is bonded to an outer layer of absorbent material 46 perforated with a multitude of small holes 48. Holes 48 give the material a wicking effect, permitting evaporation of water condensing in the intermediate layer at the polyethylene interface so that the outside of the ice pack does not become wet and unsuitable for reuse because of condensation. Rayon polyester fiber provides a suitable absorbent material for use in this application.

Ice pack 10 is constructed by positioning strips of three ply material 40 of the type shown in FIG. 3 in overlapping relation. Envelope 12 is first formed by sonically welding the first and second strips together along the seam 49. Next, bag 30 is formed internally of the envelope by sonically welding the two sheets of three ply material together along seam 32. The ice packs are then cut out by means of an automatic cutting machine in the pattern shown in FIG. 2, such that tie strings 26 and 28 are offset inwardly of the outer edge permitting tie strings 22a and 24a of the left adjacent envelope to be simultaneously cut out. Likewise, tie strings 26b and 28b of the right adjacent envelope are cut out simultaneously with tie strings 22 and 24 to eliminate wasting material between adjacent envelopes.

Referring now to FIG. 4, the closure member 50, employed for sealing the bag after it has been filled with ice, is shown in its operating position in FIG. 2. Closure member 50 contains an elongate blade-like member 52 hingedly connected to an elongate sheath member 54 by means of a flexible element 56, which may be a simple flexible plastic connection.

Blade-like member 52 is a substantially planar elongated member having inwardly inclined end surfaces 58 and 60 and containing a reinforcing rib 62 extending along the base thereof slightly beyond end surfaces 58 and 60. A cut 64 is provided in blade-like member 52 proximate the end surface 60 to provide end surface 60 with inward flexibility upon compression when blade-like member 52 is brought into registration with sheath member 54. A notch 66 is cut into the end surface 60 opposite the hinge to provide a locking structure for engaging latching structure on sheath member 54 when blade-like member 52 is brought into registration therewith.

Sheath member 54 is formed of two substantially planar sidewalls 68 connected together by a roof portion 70 and having open end surfaces over 72 and 74, which permit portions of end surfaces 58 and 60 of blade-like member 52 to extend slightly therefrom. Sheath member 54 has a length slightly less than blade-like member 52 such that some compression of end surface 60 is required to bring blade-like member 52 into registration with sheath member 54. Sheath member 54 has sufficient width between sidewalls 68 such that the envelope may be wrapped around both sides of blade-like member 52 and the blade-like member and envelope compressed into sheath member 54. Longitudinal ribs 76 and vertical ribs 78 may be provided with sidewalls 68 to further enhance the structural integrity of the closure members to render it suitable for multiple use. A flange 80 extends along the base of sidewalls 68 just beyond end surfaces 72 and 74 to define an apertured latching member 82 which cooperates with notch 66 on blade-like member 52 to lock blade-like member 52 into registration with sheath member 54.

In operation, closure member 50 is positioned against one side of ice pack 10, as shown in FIG. 2, adjacent the throat 34, such as by means of a piece of scotch tape, to hold blade-like member 52 into proper position. The outer portion of throat 34 is then folded over blade-like member 52 and blade-like member 52 is brought into registration with sheath member 54. Because sheath member 54 has a width slightly less than blade-like member 52, surface 60 will be compressed as the end surface 72 of sheath member 54 slides therealong to the point wherelatching member 82 passes into notch 66. At this point, the end surface 60 slips into the aperture in latching member 82 and the compression force on the end surface is released, thereby bringing the latching member 82 and the notch 66 into locking position. Blade-like member 52 is released from sheath member 54 by application of downward pressure to latching member 82, which forces end surface 60 inwardly of the blade-like member 52, thereby permitting sheath member 54 to slide off of end surface 60.

Figure 5:
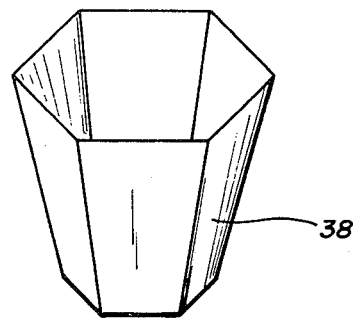
FIG. 5 is a perspective view of the funnel.

FIG. 5 shows a collapsible funnel 38 adapted to be employed in connection with the ice pack 10. In the preferred embodiment, funnel 38 is hexagonal in cross section and has an angle of convergence substantially the same as the diverging walls of throat 34 in the bag. Funnel 38 can be made of inexpensive water resistant material designed for a single use, such as cardboard. The hexagonal structure permits the funnel to be collapsed relatively flat and inserted into the bag flat prior to filling of the ice pack for ease of shipment and storage. Funnel 38 can be expanded by simple application of pressure thereto around the throat and discarded after use. The use of a polygonal cross sectional structure has also been found to facilitate the flow of ice into throat 34 as it accumulates in the funnel.

The collapsible funnel 38 is designed for a single use and may be opened and inserted in the mouth of ice pack 10 to prevent contact between the ice machine and scoop and the pack. The funnel is then discarded after use and the closure member is applied to throat 34. If a refilling of ice pack 10 is desired, the closure member may be opened, the contents of the bag poured therefrom and a second funnel 38 inserted therein to permit refilling without bringing the used ice pack into contact with the source of ice.

Ideally, the ice packs may be packaged flat with the funnel 38 inserted into throat 34 and closure member 50 taped to the outside of the ice pack. This provides a convenient means for shipping and storing the ice pack. Additional funnels 38 may be employed in connection with the ice pack to render it adaptable to multiple use for a single patient.

Whereas the present invention has been described with respect to specific embodiments thereof, it is to be understood that various changes and modifications will be suggested to one of ordinary skill in the art and it is intended to encompass such changes and modifications as fall within the scope of the appended claims.

We claim:

1. A method for constructing an improved ice pack comprising the steps of:

positioning in overlapping relation first and second strips of three ply material of the type having an inner layer of waterproof material, an intermediate layer of absorbent material and an outer layer of absorbent material perforated by a number of tiny holes;

ultrasonically welding said first and second strips together along two sides thereof and along one end thereof to form an envelope;

ultrasonically welding said first and second strips together interiorly of said envelope to form a bag member being open at the open end of said envelope and closed on all other sides;

cutting out a portion of said material outside of the closed end of said envelope such that a pair of tie strings are formed internally of the edges of said envelope in parallel relation therewith; and cutting out a portion of said material adjacent said open end to form a pair of tie strings extending from the open end of the envelope coincident with the sides thereof.

2. The method of claim 1 further comprising the step of:

sonically welding the edges of the bag member adjacent the open end of the envelope such that said bag member diverges outwardly at a selected angle.

* * * * *

UNITED STATES PATENT AND TRADEMARK OFFICE
CERTIFICATE OF CORRECTION

PATENT NO. : 4,385,950

DATED : May 31, 1983

INVENTOR(S) : Vance M. Hubbard, et al.

It is certified that error appears in the above-identified patent and that said Letters Patent is hereby corrected as shown below:

Column 4, line 46, "the point wherelatching" should be -- the point where latching --.

Column 6, line 18, "a portion of said material adjacent" should be -- a portion of said first and second strings adjacent --.

Signed and Sealed this

Sixth Day of December 1983

[SEAL]

Attest:

Attesting Officer

GERALD J. MOSSINGHOFF

Commissioner of Patents and Trademarks